United States Patent [19]
Nelson

[11] Patent Number: 4,462,872
[45] Date of Patent: Jul. 31, 1984

[54] METHOD OF OPERATING A GAS ANALYZER AND SOLID ELECTROLYTE GAS SENSING APPARATUS

[75] Inventor: Robert L. Nelson, Orrville, Ohio
[73] Assignee: Westinghouse Electric Corp., Pittsburgh, Pa.
[21] Appl. No.: 442,073
[22] Filed: Nov. 16, 1982

Related U.S. Application Data

[63] Continuation-in-part of Ser. No. 294,951, Aug. 21, 1981, abandoned.

[51] Int. Cl.³ .............................................. G01N 27/58
[52] U.S. Cl. ................................... 204/1 T; 204/410; 204/427; 204/428
[58] Field of Search ............... 204/410, 427, 428, 429, 204/1 S

[56] References Cited

U.S. PATENT DOCUMENTS

| | | | |
|---|---|---|---|
| Re. 28,792 | 4/1976 | Ruka et al. | 204/1 T |
| 4,098,650 | 7/1978 | Sayles | 204/1 T |
| 4,284,487 | 8/1981 | Barnes et al. | 204/408 |

*Primary Examiner*—G. L. Kaplan
*Attorney, Agent, or Firm*—T. R. Trempus

[57] ABSTRACT

The reference gas of an electrochemical cell is vented into the process gas being measured at a location sufficiently close to the cell to maintain the gas pressure of the reference gas equal to the gas pressure of the process gas. A packing gland for securing a sensor cell within a support member for high temperature applications is also disclosed.

9 Claims, 3 Drawing Figures

METHOD OF OPERATING A GAS ANALYZER AND SOLID ELECTROLYTE GAS SENSING APPARATUS

CROSS-REFERENCE TO RELATED APPLICATION

This application is a continuation-in-part of Application Ser. No. 294,951 filed Aug. 21, 1981 by the present inventor and owned by the present assignee and now abandoned.

BACKGROUND OF THE INVENTION

The ion conductivity of numerous solid electrolyte materials has resulted in the application of solid electrolyte electrochemical cells for numerous gas measuring applications. Solid electrolyte compositions have been incorporated in gas sensing apparatus to measure oxygen, combustibles, pollutants, i.e. $SO_2$, $CO_2$, etc. and have provided a basis for product ranging from medical instrumentation to industrial process and stack gas analyzers. A solid electrolyte electrochemical cell develops an electrical signal, current or voltage, on the basis of ion conductivity which is a function of the content of a particular gas species of interest within a monitored gas environment. The application of a solid electrolyte electrochemical cell exhibiting oxygen ion conductivity to monitor the oxygen content of a gas environment is described in detail in U.S. Pat. No. Re. 28,792 which is assigned to the assignee of the present invention and incorporated herein by reference. The solid electrolyte electrochemical cell, which consists of an oxygen ion conductive solid electrolyte having a sensing electrode disposed on one surface and a reference electrode disposed on an opposite surface, develops an EMF signal in accordance with the Nernst equation in response to a difference in the oxygen partial pressure between the sensing and reference electrodes. In order to eliminate the oxygen partial pressure at the reference electrode as a variable in the equation, a stable or known oxygen reference environment is maintained in contact with the reference electrode. This reference environment is isolated, through appropriate sealing means, from the measured gas environment contacting the sensing electrode. The same basic mode of operation of a solid electrolyte electrochemical cell as employed for the measurement of combustibles is described in U.S. Pat. No. 4,158,166, which is assigned to the assignee of the present invention and incorporated herein by reference. In this embodiment, the electrochemical cell is operated in a pumping mode to introduce oxygen from the reference source to combustibly react with combustible constituents at the sensing electrode with the cell current developed as a result of the ion conductivity providing an indication of the combustibles content of a measured gas environment. The application of solid electrolyte electrochemical cells employing a stable reference gas environment for developing an EMF signal indicative of pollutants such as $SO_2$, $CO_2$, $NO_2$, etc. is described in detail in issued Canadian Pat. Nos. 1,002,599 and 1,040,264 which are assigned to the assignee of the present invention and incorporated herein by reference.

The sealing, or isolation, of the measured gas environment from the reference gas environment poses significant practical problems in developing a trouble-free gas-sensing apparatus due to the fragile nature of the ceramic material comprising the solid electrolyte element. This problem is further compounded when developing a high temperature solid electrolyte gas-sensing apparatus, particularly when it is intended for monitoring the gas constituents of an industrial corrosive environment.

Typically, the commercial products presently available addressed this problem in one of two ways. In a first approach, the electrolyte material is limited to a relatively small disc-shaped solid electrolyte element having electrodes disposed on opposite surfaces thereof with the electrochemical cell then being sealed within a relatively strong mechanical tubular housing by an appropriate bonding technique, i.e., brazing. This minimizes the chances for mechanical fracture of the ceramic material but poses potential gas leaks through the seal. A second approach is to utilize a closed end solid electrolyte tube with the electrodes being disposed on opposite surfaces of the closed end. The tube extends into a relatively cool and friendly environment before a transition is made through a flange or an adapter. This approach essentially eliminates the seal problem but exposes the fragile ceramic material to mechanical damage.

Another drawback encountered in presently available commercial products is the combination of rigid and flexible tubing employed to introduce the reference gas to the electrochemical cell and to exhaust the spent reference gas from the sensor apparatus. The flexible tubing is subject to gas leaks, particularly where mated to the rigid tubing, and to thermally induced damage.

It is an object of this invention to provide a gas sensing apparatus which vents the reference gas from the sensing apparatus into the process gas region thus eliminating the flexible tubing and hermetic seals, heretofore common in commercially available products.

SUMMARY OF THE INVENTION

There is disclosed herein with reference to the accompanying drawings a technique for minimizing the adverse affects of seal leaks and solid electrolyte material fracture in solid electrolyte electrochemical cell gas measuring apparatus. In the prior art gas analyzer configurations employing a flowing reference gas environment the flowing reference gas is exhausted from the electrochemical cell gas sensor at a location remote from the solid electrolyte electrochemical cell. It has been determined experimentally that if the flowing reference gas is vented from the solid electrolyte electrochemical cell assembly to the measured gas environment at a location which is close to the electrochemical cell, the gas pressure across the solid electrolyte electrochemical cell will be essentially equalized. The equalization of the gas pressure across the electrochemical cell minimizes the likelihood of leakage between the gas environments contacting the sensing and reference electrodes of the electrochemical cell and eliminates potential back pressures which could result in mechanical fracturing of the solid electrolyte element. This equalization of total gas pressures on either side of the solid electrolyte element further eliminates the requirement for adjusting the pressure of the reference gas environment to approximate that of the measured gas environment in order to assure the validity of the gas measuring electrical signal developed by the solid electrolyte electrochemical cell. This disclosed technique essentially eliminates the need for employing a long fragile closed and solid electrolyte tube in one gas apparatus design approach, and the difficult high temperature sealing requirements of the combination of a solid electrolyte cell and a mechanical supporting tube.

While the novel reference gas vent technique has particular application to gas sensors employing solid electrolyte electrochemical cells, the concept is also applicable to electrochemical cell gas analyzers using a gel or liquid electrolyte.

BRIEF DESCRIPTION OF THE DRAWINGS

The invention will become more readily apparent from the following exemplary description in connection with the accompanying drawings.

DESCRIPTION OF THE PREFERRED EMBODIMENT

In a typical commercially available solid electrolyte gas analyzer using a flowing reference gas, the reference gas is supplied to the reference electrode of the solid electrolyte electrochemical cell and subsequently vented to an atmosphere remote from the process gas environment being measured by the solid electrolyte gas analyzer. It has been determined experimentally, that if the reference gas is vented, or discharged, to the process, or monitored, gas environment at a location relatively close to the solid electrolyte electrochemical cell, the pressure of the reference gas contacting the reference electrode of the solid electrolyte electrochemical cell can be maintained essentially equal to the pressure of the process gas contacting the sensing electrode. This is accomplished regardless of variations in the process gas pressure. This technique not only eliminates the error during voltage mode operation in the electrochemical cell signal caused by process gas pressure variations, but also reduces the pressure drop across the ceramic solid electrolyte sensor sufficiently to minimize the gas leakage between the process gas and the reference gas environments in both the voltage mode and the current mode. The reference gas vent is located so as not to alter the process gas in the vicinity of the sensing electrode of the electrochemical cell. Similarly, if the gas analyzer provides for introducing test or calibration gases to the sensing electrode of the electrochemical cell it is necessary to locate the reference gas vent so as to avoid mixing the vented reference gas with the calibration or test gas. Typical embodiments of solid electrolyte gas analyzers incorporating the novel reference vent technique are described below with reference to the illustrations of FIGS. 1 and 2.

Figure 1:
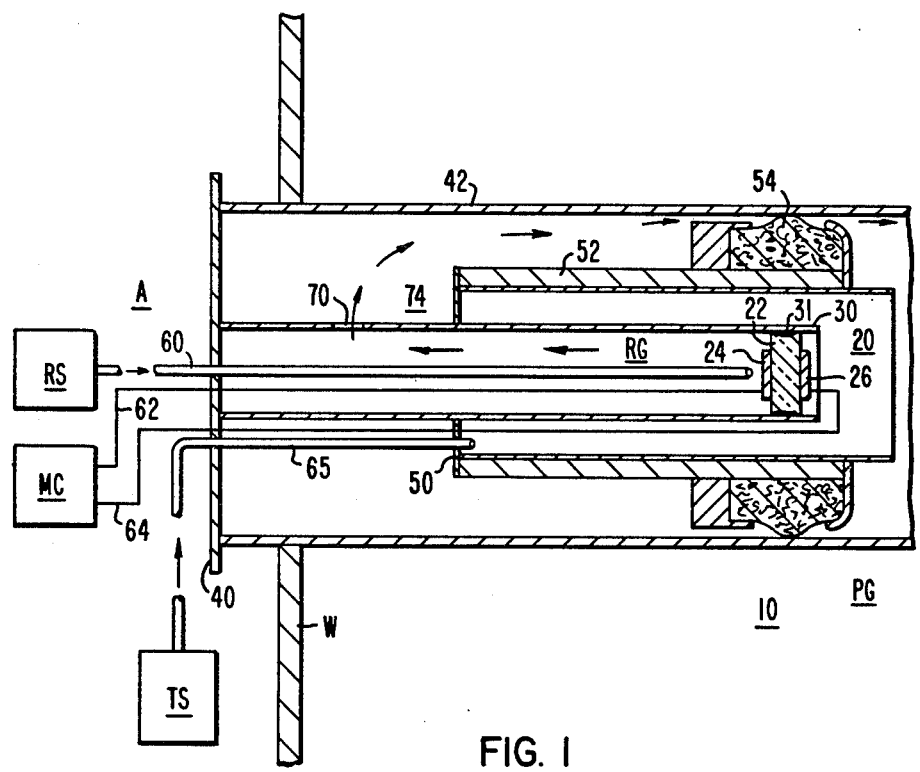
FIG. 1 is a sectional schematic illustration of an in-situ gas sensing device employing the invention.

In the industrial probe-type solid electrolyte gas analyzer 10 illustrated in FIG. 1, a disc-shaped solid electrolyte electrochemical concentration cell 20 is sealed within a support tube 30 via a seal 31. The support tube 30, which may be typically a metal member, passes through a first bulk head member 40 and a second bulk head 50. The second bulk head 50 includes a tubular member 52 which supports an annular porous dust seal 54 which contacts an outer tubular shield member 42 extending from the bulk head 40. The porous seal 54 reduces the passage of particulate material from the process gas environment PG into the gas analyzer assembly 10. The tubular protective shield 42 is secured within an opening of the wall W of the process gas enclosure which may typically be a stack in an industrial environment. The solid electrolyte electrochemical cell 20, as described in the above-referenced patents, consists of an ion conductive solid electrolyte element 22 having a reference electrode 24 and a sensing electrode 26 disposed on opposite surfaces thereof. The composition of the solid electrolyte member 22 is selected so as to render the cell 20 responsive to a particular gas constituent of interest in the process, or monitored gas, gas environment PG. The gas constituent of interest may be oxygen, a combustibles constituent, a pollutant constituent, etc. A known or stable reference gas environment RG is maintained in contact with the reference electrode 24 by flowing a reference gas at a controlled rate from a remote reference gas source RS through an inlet tube member 60. The electrical signal developed by the electrochemical cell 20 in response to the partial pressure of the gas constituent of interest of the process gas environment PG is monitored by a remote measuring circuit MC connected to the electrodes 24 and 26 via electrical leads 62 and 64. In the event in-situ calibration of the electrochemical cell 20 is required, a test gas inlet tube 65 is provided for supplying a calibration gas within the tubular member 52 from test gas source TS for contacting the sensing electrode 26. The gas sensing assembly described thus far is indicative of commercially available gas analyzer probe assemblies. The commercially available analyzers vent the reference gas to the atmosphere A, remote from the process gas environment PG. In the embodiment of FIG. 1 a reference gas vent 70, illustrated as an aperture in the support tube 30, provides for the venting of the reference gas from the reference gas environment RG through the annular chamber 74 defined as the space between the tubular members 30 and 42, through the porous seal 54 and into the process gas environment PG as indicated by the arrows. The location of the vent 70 assures the passage of the reference gas into the process gas environment PG without diluting or interfering with the gas composition of the process gas environment or the test gas at the sensing electrode 26 of the electrochemical cell 20. The venting of the reference gas from a vent location 70 in close proximity to the electrochemical cell 20 into the processed gas environment PG achieves the benefits of gas pressure equalization across the solid electrolyte electrochemical cell 20 for a predetermined reference gas flow rate. The reference gas flow rate is set such that the difference in gas pressure between the reference gas environment RG and process gas environment PG across the cell 20 corresponds to the pressure drop established by the reference gas vent path, i.e., vent 70. The gas pressure of the reference gas environment RG is thus maintained essentially equal to the gas pressure of the processed, or monitored, gas environment. Further, in the embodiment illustrated in FIG. 1, the pressure drop across vent 70 created by the reference gas flow rate results in the reference gas functioning as a purge gas to prevent corrosive gases of the process gas environment PG from entering this area of the assembly 10.

Figure 2:
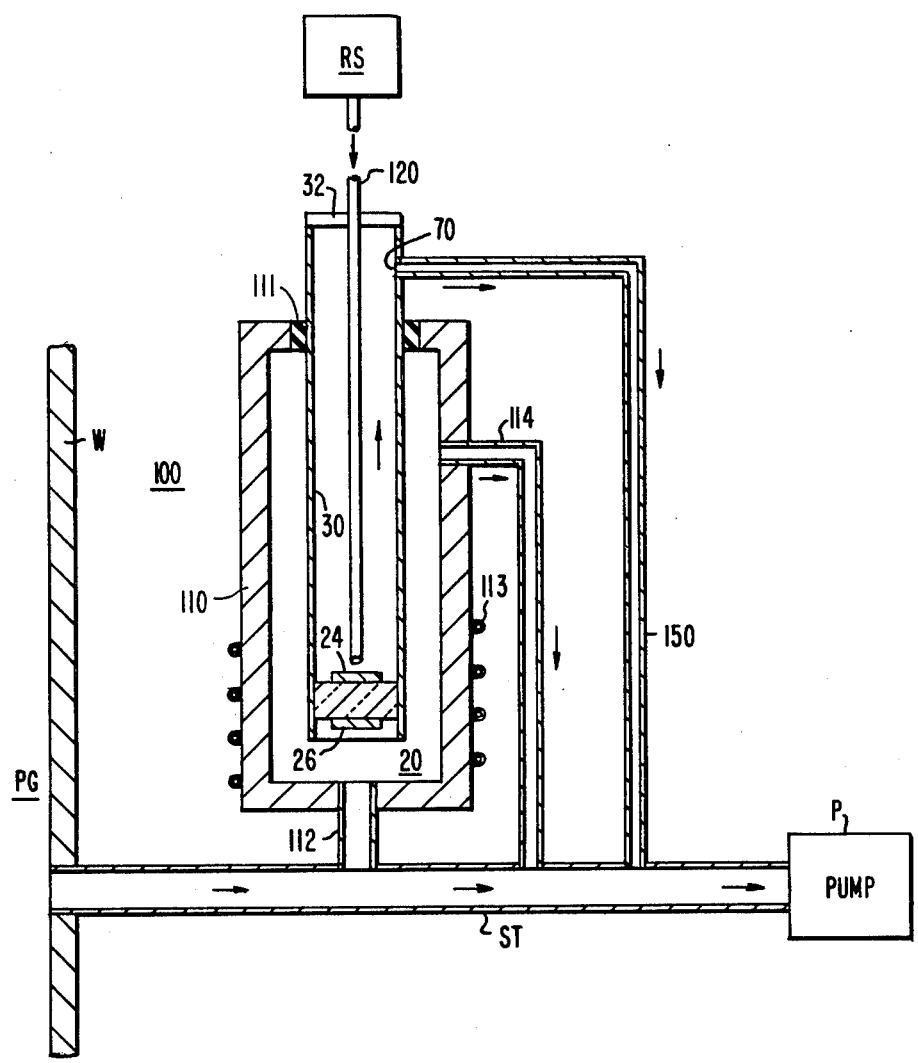
FIG. 2 is a sectional schematic illustration of an externally mounted gas sensing device employing the invention.

While the embodiment of FIG. 1 illustrates a gas analyzer probe assembly for the in-situ measurement of the gas constituent of a process gas environment, the gas analyzer 100 of FIG. 2 is mounted outside the process gas environment PG. It responds to a sample of the process gas drawn through a sample tube ST to provide a measurement of the partial pressure of a gas constituent of interest of the process gas PG. A combination of a disc-shaped solid electrolyte electrochemical cell 20 sealed within a tubular support member 30, comparable to that described above with reference to FIG. 1, is sealed within a tubular housing 110 through the use of a seal member 111. A pump P draws a sample of the process gas into the sample gas flow tube ST. An inlet tube 112, which provides gas flow communication between the sample gas flow tube ST and the internal volume of the housing 110 exposes a sensing electrode 26 of the electrochemical cell 20 to a sample of the process gas environment PG. The sample gas is then drawn from the internal volume of the housing 110 through the output tube 114 back into the sample flow tube ST. A flowing reference gas is brought into contact with the reference electrode 24 of the electrochemical cell 20 via a reference gas inlet tube 120 which enters the support tube 30 through a gas seal 32. The reference gas flow is supported by the action of the pump P which draws the reference gas from the support tube 30 through a reference gas exhaust tube 150 and introduces the exhaust reference gas into the sample gas flow tube ST at a location slightly downstream from the sample gas inlet tube 112. The coupling of the exhaust reference gas from the reference gas environment of the cell 20 to the sample gas flow tube ST at a location slightly downstream from the sample gas inlet tube 112 avoids mixing of the reference gas with the sample gas being measured by the cell 20. It is however sufficiently close to the inlet tube 112 so as to achieve the desired gas pressure equalization across the electrochemical cell 20 to realize the objectives defined above. The conventional need for a leak-tight seal between the sensing electrode surface of the electrochemical cell 20 and the reference electrode surface of the electrochemical cell 20 is minimized through the use of the reference gas vent technique illustrated in FIGS. 1 and 2 due to the fact that the total gas pressure difference across the electrochemical cell 20 is held to a value equal to the pressure drop through the reference gas vent path as determined by controlling the reference gas flow rate.

Figure 3:
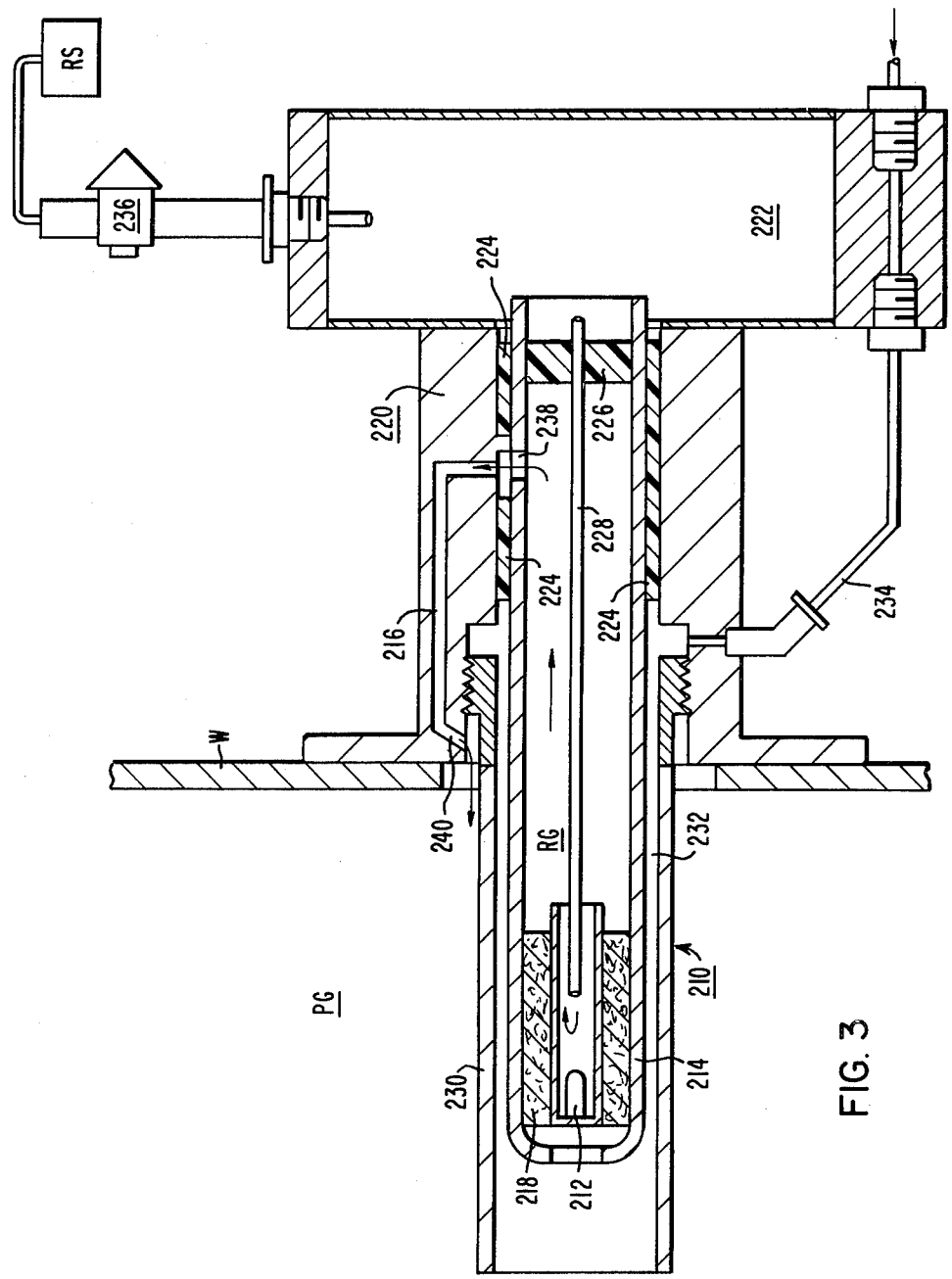
FIG. 3 is a sectioned schematic illustration of a high temperature probe-type gas sensing device, all according to the teachings of this invention.

An industrial probe-type solid electrolyte gas analyzer according to this invention which is particularly well suited for high temperature applications is generally indicated by the reference character 210 in FIG. 3. By high temperature application, it is understood that the environment to which the solid electrolyte electrochemical concentration cell 212 is exposed can be up to about 3000° F. As previously indicated, severe operational and structural problems are encountered in such a hostile environment. The embodiment described in connection with FIG. 3 not only eliminates the error caused by process gas pressure variations but also reduces the pressure drop across the sensor cell 212 when operated in the voltage mode. As a result, it is not necessary to provide a leak free seal between the cell 212 and the cell supporting member 214. The elimination of the requirement of such seals is particularly beneficial in high temperature operations. Since different materials are utilized in the sensor construction it has been extremely difficult to provide a seal or bond capable of withstanding the mechanical stress resulting from differing thermal expansion rates.

An effective, thermal impact resistive probe structure for high temperature operations is provided through the use of the reference gas vent 216 and the packing gland 218 features of this invention. The gas analyzer 210 includes a housing portion 220 which secures the probe 210 to wall "W" of the process gas enclosure. The housing portion 220 is preferably stainless steel. A pressurized reference gas chamber 222 extends from one end of the housing 220 and the sensor cell structure 212 and associated structural members project from the other end of the housing. The support member 214 which is preferably an aluminum tube is secured in the housing 220 by securing means such as ceramic cemented joints 224. An internal ceramic joint 226 supports and seals a reference gas inlet tube 228 within the support member 214. The tubular cell structure 212 is mounted at the other end of the support member 214 by the packing gland 218. The gland 218 and the cemented joints 226 define the reference gas RG zone of the gas analyzer 210. The gland 218 is a material characterized by both its stability at high temperatures as well as its flexibility in absorbing the aforedescribed thermally induced mechanical stress between the sensor cell and the support member. A preferred material from which the gland 218 is formed is saffil wool that is packed between the support member 214 and the cell structure 212. Powdered zirconium oxide or aluminum oxide is poured into the wool packing and fused. The gland 218 is substantially resistant to gas flow therethrough. An outer tube 230 protects the cell 212 from the erosive effect of particulate in the process gas and defines a test gas conduit 232 circumferentially disposed about the cell 212. A test gas inlet tube 234 feeds a calibration gas to the conduit 232 from a test gas source TS.

The reference gas is provided from a pressurized source RG through regulator 236 where reference gas pressure is maintained at a predetermined level. The reference gas RG enters the chamber 222 where it passes through inlet tube 228 prior to contacting the cell 212. After contacting the cell 212 the reference gas circulates from the sensor end of the analyzer back toward the housing 220 as indicated by the several arrows. The reference gas is then vented to the process gas environment PG through an aperture 238 in the support member 214 and outlet 240 of the housing 220. The reference gas is maintained at a flow rate such that the gas pressure difference between the reference gas environment and the monitored gas environment across the cell is substantially equal to the pressure drop across the reference gas vent means. As can be seen in FIG. 3, the ceramic joint securing means 224 isolates the reference gas vent 216 from the test gas conduit 232. Moreover, the isolation of the test gas conduit 232 from both the reference gas supply RG and the reference gas vent 216 eliminates the heretofore common practice of using flexible tubing mated to rigid tubing as feeder lines for the various gas supplies disposed at one end of the gas analyzer. The separate reference gas vent 216 and test gas conduit 232 make it practicable to utilize the chamber 222 as a reference gas feed means which substantially encloses one end of the analyzer, and to provide a simplified ceramic joint arrangement as at 224 and 226.

The location of the vent 216 assures the passage of the reference gas into the process gas environment without diluting or interfering with the gas composition of the process gas environment or the test gas. Additionally, the vent 216 maintains the pressure difference across the sensor cell 212 at very low values regardless of variations in process gas pressure. As a result, the gas analyzer 210, operating in the voltage mode, can accurately measure the percentage of a particular constituent of interest in the process gas under all process gas pressure conditions without correcting for static pressure changes.

The high temperature gas analyzer 210 which utilizes the reference gas venting technique and the unique packing gland 218 which separates the process gas from the reference gas, permits the use of a relatively short sensor cell 12 mounted within a support member made of sturdy, thermally shock resistant material without the requirement of a hermetic seal. Moreover, the gas analyzer 210 utilizes a reference gas feed chamber 222 which in combination with the reference gas vent 216 eliminates the use of flexible tubing and simplifies sensor apparatus structure.

What has been described is a reference gas venting technique for industrial gas analyzers of both the probe-type and the externally mounted type. Additionally, the present reference gas venting technique together with a sensor-supporting packing gland permit high temperature in-situ process gas analysis.

What is claimed is:

1. In a method for operating a gas analyzer apparatus including the steps of venting flowing reference gas and equalizing the pressure of said flowing reference gas environment and a monitored gas environment disposed in contact with either side of a gas measuring electrochemical cell mounted in a support member defining said reference gas environment, said support member being received in a tubular shield member, an annular chamber being defined therebetween, and including a porous seal separating the annular chamber from the monitored gas environment; the improvement to said method comprising the steps of:

venting the flowing reference gas from the reference gas environment in the support tube into the annular chamber at a venting location sufficiently close to the electrochemical cell to make the gas pressure of the reference gas environment substantially equal to the gas pressure of the monitored gas environment, said venting location being selected to prevent the vented reference gas from affecting the measurement of the monitored gas environment by said electrochemical cell;

adjusting the flowing reference gas flow rate to provide a difference in gas pressure between the reference gas environment and the monitored gas environment which difference corresponds to a pressure drop established by said venting location; and purging both said annular chamber and said porous seal of gas from the monitored gas environment with said vented flowing reference gas.

2. In an in-situ gas analyzer apparatus having reference gas vent means to vent a flowing reference gas from a reference gas environment to a monitored gas environment, the improvement wherein said gas analyzer apparatus comprises:

an electrochemical cell for generating an electrical signal in either a voltage mode or a current mode indicative of a gas constituent of interest of a monitored gas environment on the basis of a difference in the partial pressure of the gas constituent of the monitored gas environment contacting one surface of the electrochemical cell and that of the flowing reference gas environment contacting the opposite surface of the electrochemical cell;

a tubular support means;

a packing gland means securing said electrochemical cell within said tubular support means, said gland means being substantially resistant to gas flow therethrough, while resiliently accommodating mechanical stress between said cell and said tubular support means, said gland means separating said reference gas environment within said tubular support means from said monitored gas environment at said cell;

a housing portion having securing means therein for retaining the tubular support means within said housing portion; said housing portion having an aperture therein defining the reference gas vent means, said aperture being in communication with said tubular support means at a location sufficiently close to the cell to make the gas pressure of the reference gas environment substantially equal to the gas pressure of the monitored gas environment; and means for maintaining a reference gas flow rate such that gas pressure difference between the reference gas environment and monitored gas environment across said cell is substantially equal to the pressure drop across said reference gas vent means.

3. The gas analyzer apparatus according to claim 2 wherein the packing gland means comprises saffil wool and zirconium oxide powder fused therein.

4. The gas analyzer apparatus according to claim 2, wherein the reference gas vent means is defined by an aperture in said housing portion and said securing means.

5. The improved gas analyzer apparatus according to claim 2 including an outer tubular member extending from the housing portion and mounted in a spaced relation about said tubular support means, defining therebetween a test gas conduit adapted to deliver test gas to the process gas environment side of said electrochemical cell.

6. The gas analyzer apparatus according to claim 5 including test gas supply means in communication with the test gas conduit for delivering test gas to the process gas environment side of the electrochemical cell.

7. The gas analyzer apparatus according to claim 6 wherein the securing means isolates the reference gas vent means from the test gas conduit.

8. The gas analyzer apparatus according to claim 7 wherein the housing portion includes a reference gas chamber at the end thereof opposite the outer tubular member, said chamber substantially enclosing said housing portion opposite end; and a reference gas inlet tube in communication with said chamber for conducting reference gas from said chamber to the electrochemical cell wherein said reference gas is then vented from said gas analyzer apparatus through said reference gas vent means.

9. The gas analyzer apparatus according to claim 7 wherein the securing means are ceramic seals sealing said tubular support means within said body portion.

* * * * *